United States Patent [19]

Nelson et al.

[11] Patent Number: 4,792,551
[45] Date of Patent: Dec. 20, 1988

[54] 9-ANTHRYLOXYAMINOALKANES AND RELATED COMPOUNDS AS ANTI-INFLAMMATORY AND ANALGETIC AGENTS

[75] Inventors: Peter H. Nelson, Los Altos; Stefan H. Unger, Palo Alto, both of Calif.; Thomas R. Thieme, Independence, Oreg.

[73] Assignee: Syntex (U.S.A.) Inc., Palo Alto, Calif.

[21] Appl. No.: 514,112

[22] Filed: Jul. 15, 1983

[51] Int. Cl.$^4$ .................. A61K 31/135; A61K 31/205
[52] U.S. Cl. .................................... 514/651; 540/450; 544/155; 544/380; 546/204; 548/575; 548/950; 514/157; 514/210; 514/211; 514/255; 514/555; 514/239.2; 564/352
[58] Field of Search ............... 564/352, 379; 424/330, 424/316; 260/501.18

[56] References Cited

U.S. PATENT DOCUMENTS

| | | | |
|---|---|---|---|
| 3,227,716 | 1/1966 | Harms | 564/352 X |
| 3,304,307 | 2/1967 | Mizzoni | 564/379 X |
| 3,422,106 | 1/1969 | Boissier et al. | 564/352 X |
| 3,493,616 | 2/1970 | Symon | 564/387 X |
| 3,579,582 | 5/1971 | Symon | 564/387 X |
| 3,816,430 | 6/1974 | Santilli et al. | 564/352 |
| 4,127,717 | 11/1978 | Hauck et al. | 564/379 X |

Primary Examiner—Robert V. Hines

Attorney, Agent, or Firm—Tom M. Moran; Ellen J. Wise; Alan M. Krubiner

[57] ABSTRACT

Compounds useful for treating inflammation, pain and swelling, represented by the formula:

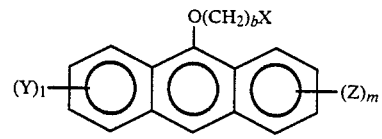

and the pharmaceutically acceptable acid addition salts thereof, wherein:

Y and Z are each independently halo, alkyl or alkoxy;
l and m are each independently integers of 0-4;
b is an integer of 2-12; and
X is selected from the group consisting of:
  $-NR^1R^2$, $-NR^1(CH_2CH_2OH)$,

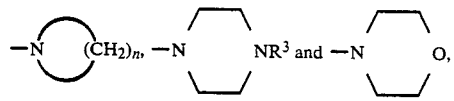

in which
$R^1$ and $R^2$ are independently H, alkyl or cycloalkyl;
$R^3$ is H, alkyl or $CH_2CH_2OH$; and
n is an integer of 3–7.

15 Claims, No Drawings

9-ANTHRYLOXYAMINOALKANES AND RELATED COMPOUNDS AS ANTI-INFLAMMATORY AND ANALGETIC AGENTS

BACKGROUND OF THE INVENTION

This invention concerns anti-inflammatory and analgetic agents which are 9-anthryloxyaminoalkanes.

Anti-inflammatory and analgetic activity has been demonstrated by compounds representing a variety of structural classes, including, for example, the corticosteroids, aspirin and related compounds, derivatives of arylacetic and arylpropionic acids, and relatives to phenylbutazone. However, no repesentative of any of these classes of compounds is regarded as ideal.

It has now been discovered that certain 9-anthryloxy aminoalkanes and related compounds exhibit useful anti-inflammatory and analgetic activity.

Compounds somewhat structurally and functionally similar to the compounds of the present invention are described in U.S. patent application Ser. No. 392,859, which discloses certain α-naphthylaminoalkylamines as antiinflammatory and analgetic agents.

SUMMARY OF THE INVENTION

One aspect of the invention concerns novel compounds of the formula

<chemical structure> (I)

and the pharmaceutically acceptable acid addition salts thereof, wherein:
Y and Z are each independently halo, alkyl or alkoxy;
l and m are each independently integers of 0-4;
b is an integer of 2-12; and
X is selected from the group consisting of:
—$NR^1R^2$, —$NR^1(CH_2CH_2OH)$, <chemical structures> in which
$R^1$ and $R^2$ re independently H, alkyl or cycloalkyl;
$R^3$ is H, alkyl or $CH_2CH_2OH$; and
n is an integer of 3-7.

In two other aspects, the invention relates to pharmaceutical compositions containing a compound of Formula I and to methods of preventing, reducing or inhibiting inflammation and associated pain with compounds of Formula I or the aforesaid pharmaceutical compositions.

Finally, the invention relates to a process for the preparation of compounds of Formula I and their salts.

DETAILED DESCRIPTION OF THE INVENTION

Definitions

As used herein:

"Alkyl" means a branched or unbranched saturated hydrocarbon chain containing 1-8 carbon atoms, such as methyl, ethyl, propyl, isopropyl, tert-butyl, butyl, n-hexyl, n-heptyl or iso-octyl and the like.

"Alkoxy" means the group —OR wherein R is alkyl as herein defined.

"Cycloalkyl" means a saturated carbocyclic ring containing 5-7 carbon atoms.

"Optional" or "optionally" means that the subsequently described event or circumstance may or may not occur, and that the description includes instances where said event or circumstance occurs and instances in which it does not. For example, "optionally substituted anthraquinone" means that the anthraquinone may or may not be substituted and that the description includes both unsubstituted anthraquinone and anthraquinone wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

<chemical structure> means a radical, heterocyclic in structure, having one nitrogen and 3-8 carbons in the heterocyclic ring, such as azetidine, pyrrolidine, piperidine, etc.

The compounds of the invention herein contain an amino nitrogen on the alkyl side chain at which acid addition salts can be formed. "Pharmaceutically acceptable acid addition salts" refers to those salts which retain the biological effectiveness and properties of the corresponding free bases and which are not biologically or otherwise undesirable. They are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

"Anthracene nucleus" means the aromatic fused benzene ring portion of the compounds of the invention.

The numbering system for the anthracene nucleus is shown below:

<chemical structure> (I)

The "Y" substituent(s) may be positioned at any of positions 1-4 and 5-8 on the anthracene nucleus.

The compounds of the invention will be named as anthryloxyaminoalkanes. Following are examples of how representative compounds are named:

A compound of Formula I wherein b is 6, X is dimethylamino, and l and m are 0 is named "1-(9-anthryloxy)-6-dimethylaminohexane."

A compound of Formula I wherein b is 5, X is amino and l and m are 0 is named "1-(9-anthryloxy)-5-aminopentane."

A compound of Formula I wherein Y is chloro in the 6-position, l is 1, m is 0, b is 8 and X is pyrrolidine is named "1-(6-chloro-9-anthryloxy)-8-pyrrolidinooctane".

A compound of Formula I wherein Y is methoxy in the 6-position, l is 1, m is 0, b is 6 and X is hydroxyethylamino is named "1-(6-methoxy-9-anthryloxy)-6-(2-hydroxyethylamino)hexane."

METHODS OF PREPARATION

The compounds of the invention (compounds of Formula I) are prepared by procedures described below, which are illustrated by the following reaction scheme:

phthalic anhydrides bearing 0 to 4 substituents (halo, alkyl, or alkoxy) with benzenes bearing 0 to 4 similar substituents, so as to produce the expected mono- or polysubstituted benzoylbenzoic acids. The syntheses of these substituted benzoylbenzoic acids are described in detail in *Friedel-Craft and Related Reactions*, ed. by G. Olah, Vol. III, Part I, pp. 710–759. The appropriately sustituted phthalic anhydrides and benzene starting materials are commercially available or are readily prepared by standard means well known in the art.

Alternatively, the substituted anthrones of Formula A may be prepared by reduction of the corresponding anthraquinones using, for example, a metal such as tin, zinc or aluminum, and an acid such as hydrochloric,

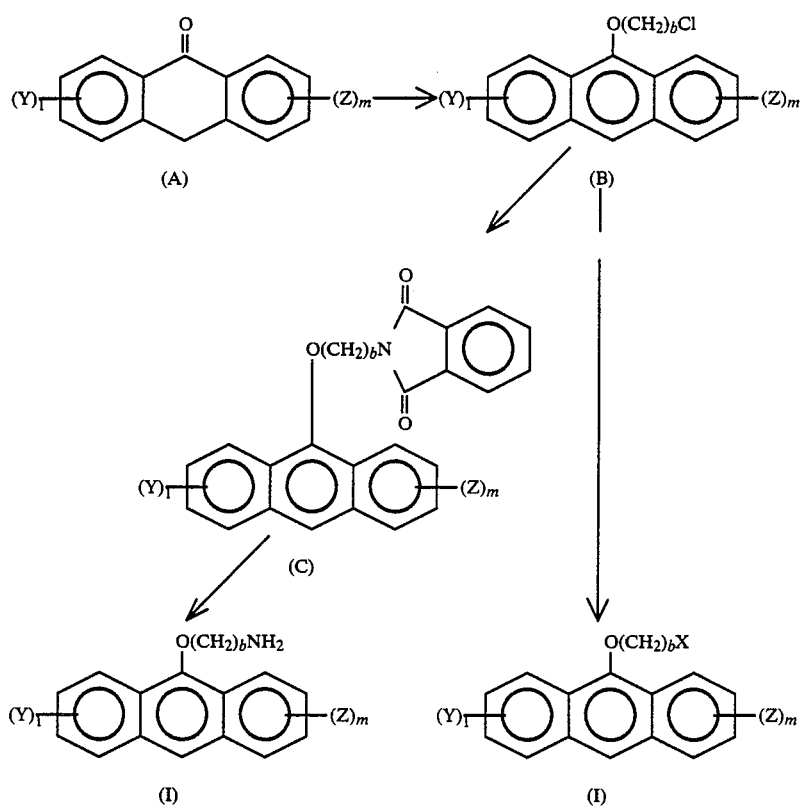

The compounds of Formula I are prepared from the corresponding optionally substituted anthrones of the formula A. Unsubstituted anthrone, as well as many of the substituted anthrone starting materials, are commercially available. Substituted anthrones can also be obtained by well known synthetic procedures described in the chemical literature. For example, substituted anthrones of Formula A can be made by cyclization of appropriately substituted benzylbenzoic acids with concentrated sulphuric acid. This method is described in greater detail in *Chemische Berichte*, 1894, 27, 2786. The appropriately substituted benzylbenzoic acids can be made in several ways, for example by reduction of the corresponding benzoylbenzoic acids using any suitable reducing agent such as, for example, zinc in acetic acid or hydrogen in the presence of a catalyst. The corresponding substituted benzoylbenzoic acids are most easily obtained by the Friedel-Craft reactions between acetic or sulphuric. The corresponding substituted anthraquinones are commercially available or can be prepared by any of several methods, such as for example, those described in *The Chemistry of Carbon Compounds*, by E. H. Rodd, First Edition, Vol. III B, p. 1384 and Second Edition, Vol III H, pp. 55–71, which also describe the reduction of the anthraquinones to the corresponding anthrones. As described in these references, substituted anthraquinones can be obtained in a variety of ways, including the Diels-Alder reactions of substituted naphthoquinones, oxidation of substituted anthracenes, and cyclization of the substituted benzoylbenzoic acids whose synthesis is described above. The synthesis of substituted benzoylbenzoic acids, and the two above-described methods of converting them to substituted anthrones, shown in the following reaction scheme, are described in greater detail in Preparations 1 and 2 hereinbelow.

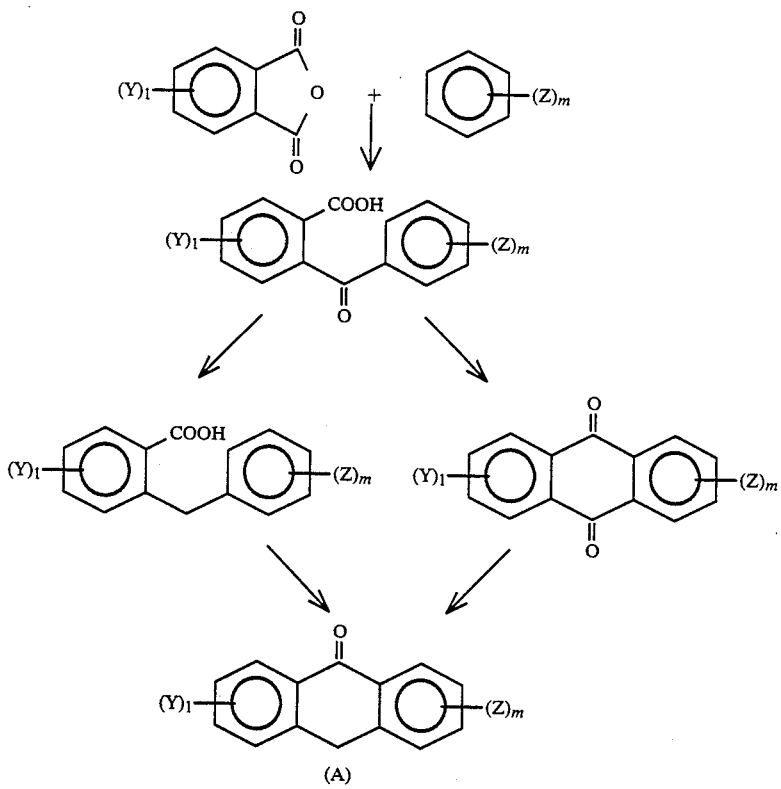

(A)

The alkoxy substituted anthraquinones and anthrones can also be obtained from the corresponding hydroxyanthraquinones and hydroxyanthrones by conventional alkylation reactions.

To prepare the compounds of the invention, the optionally substituted anthrone of Formula A is first converted to the corresponding 9-anthryloxy alkyl chloride compound of Formula B by reaction with an ω-chloroalkylsulphonate, as indicated:

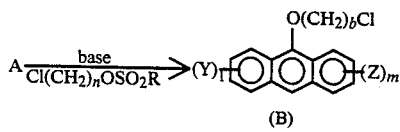

(B)

The ω-chloroalkyl sulphonate used as a reagent in the above reaction is obtained from the corresponding ω-chloroalkanol, by reaction of the alkanol with one molar equivalent of an alkyl or arylsulphonyl chloride in a basic organic solvent. The length of the alkyl chain of the ω-chloroalkanol compound determines the number (b) of carbon atoms in the alkyl chain of the anthracene ether of Formula I. Chain lengths of 2-6 carbon units are preferred, with 3 and 4 being especially preferred. The ω-chloralkanol compounds are commercially available, or can be readily prepared by reaction between an approriate α,ω-diol, such as decane 1, 10-diol, and hydrochloric acid, as described in the "Journal of the American Chemical Society", 66, 1821, 1944 and the Journal of Organic Chemistry, 18, 1356, 1953. Any suitable alkyl or arylsulphonyl chloride can be reacted with the ω-chloroalkanol to form the ω-chloralkylsulphonate. A preferred reagent is p-toluenesulphonylchloride. The reaction takes place in a basic organic solvent such as triethylamine or, preferably, pyridine, at 0°–25° C., preferably 5° C., for about 1–12, preferably about 2, hours.

The compound of Formula A is reacted with about 1.0–1.3, preferably about 1.05, molar equivalents of the chosen ω-chloroalkylsulphonate, preferbly p-toluenesulphonate, in a polar aprotic organic solvent such as tetrahydrofuran, formamide, or, preferably, N,N-dimethylformamide. The reaction takes place in the presence of from one to five molar equivalents of an inorganic base such as sodium hydroxide, or, preferably, about 5 molar equivalents of potassium carbonate. The reaction is conducted at a temperature of about 25°–125° C., preferably about 70° C., over a period of about 2–48 hours, preferably about 22–26 hours. The resulting product of Formula B, a 9-anthryloxyalkyl chloride, is isolated by conventional means.

The products of the reactions described herein can be isolated and purified by any suitable separation or purification procedure, such as, for example, filtration, extraction, crystallization, column chromatography, thin-layer chromatography, thick-layer chromatography, preparative low or high pressure liquid chromatography, or a combination of these procedures. Specific illustrations are described in the Examples. However, other equivalent separation or purification procedures can be used.

The salt products are also isolated by conventional means. For example, the reaction mixtures can be evaporated by dryness and the salts then further purified by standard methods such as those listed above.

The compounds of Formula B are then converted to the desired compounds of Formula I by treating with the appropriate reagent, as described in Sections A and B, below.

A. Compounds of Formula I

Compounds of Formula I are prepared by treating the optionally substituted compound of Formula B with the appropriate amine or compound of the formula

thereby converting the halo-group to the corresponding nitrogen containing substituent. This reaction is shown below:

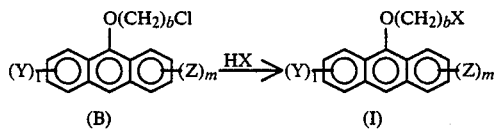

To carry out this conversion, the compound of Formula B is dissolved in and reacted with a solution of 5-25 molar equivalents of the appropriate cyclic or acyclic amine, preferably acyclic, and most preferably N,N-dimethylamine. This reaction may be performed with or without the presence of an optional polar organic solvent, water, or mixtures thereof, such as methanol, aqueous ethanol, or preferably, ethylene glycol. The reaction takes place at a temperature of about 60°-180° C., preferably about 100° C., for about 1-8 hours, preferably about 3 hours, at a pressure of about 1-5 atmospheres, preferably at atmospheric pressure. When the reaction is substantially complete, the product compound of Formula I is isolated by conventional means, and if desired, converted to a pharmaceutically acceptable salt.

B. Compounds of Formula I Wherein X is $NH_2$.

Compounds of Formula I wherein X is $NH_2$ are preferably prepared by converting the compound of Formula B to the corresponding phthalimide compound of Formula C, and then hydrolyzing the phthalimide group, as shown in the following reaction scheme:

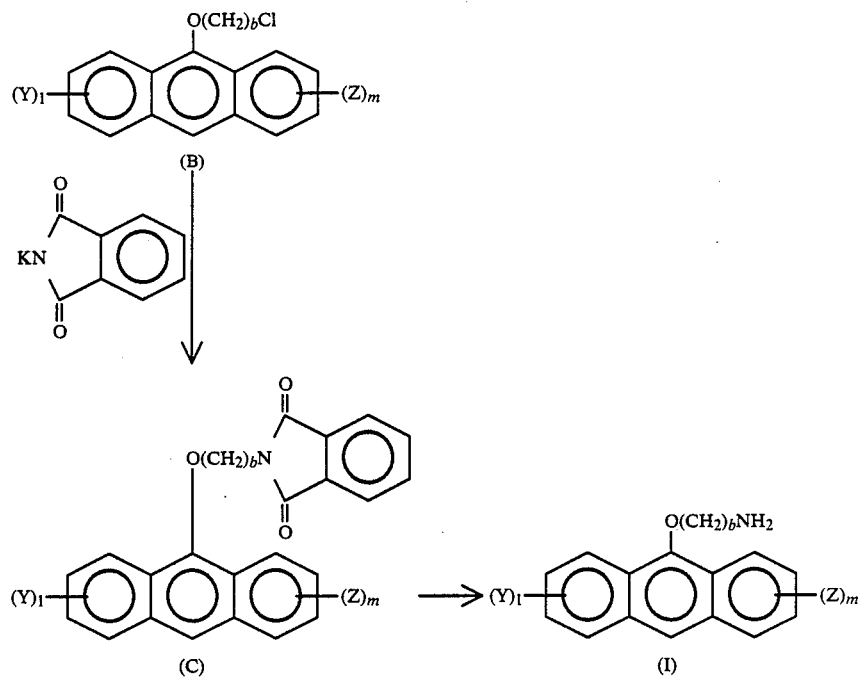

In carrying out this conversion, the compound of Formula B is dissolved in an inert aprotic organic solvent such as tetrahydrofuran, formamide, or preferably, N,N-dimethylformamide. To this solution is added about 1.0-1.5, preferably about 1.05, molar equivalents of a metal salt of phthalimide, preferably potassium phthalimide. The reaction mixture is heated to about 60°-135° C., preferably about 130° C., for 1-24 hours, preferably about 8 hours.

The product of Formula C, N-(9-anthryloxyalkyl)phthalimide, may be isolated by conventional means. It is then reacted with about 1-5, preferably about 1.5, molar equivalents of hydrazine, in a polar organic or aqueous-organic solvent such as methanol or, preferably, aqueous ethanol. The reaction is maintained at from about 25° C. to reflux temperature, preferably at reflux temperature, for about 1-12, preferably about 3, hours. The resulting optionally substituted 9-anthryloxyalkylamine compound of Formula I is then isolated by conventional means and, if desired, may be converted to a corresponding pharmaceutically acceptable salt.

C. Salts of Compounds of Formula I

All of the compounds of Formula I may be converted to their acid addition salts, by virtue of the presence of the amine terminating the alkyl side chain.

The compounds of Formula I in free base form may be converted to the acid additon salts by treating with a stoichiometric excess of the appropriate organic or inorganic acid, such as, for example, phosphoric, citric, pyruvic, hydrochloric or sulfuric acid and the like. Typically, the free base is dissolved in a polar organic solvent such as ethanol or methanol, and the acid added thereto. The temperature is maintained at between about 0° C. and 50° C. The resulting acid addition salt precipitates spontaneously or may be brought out of solution with a less polar solvent.

The acid addition salts of the compounds of Formula I may be decomposed to the corresponding free bases by treating with a stoichiometric excess of a suitable base, such as potassium carbonate or sodium hydroxide, typically in the presence of aqueous solvent, and at a temperature of between about 0° C. and 50° C. The free base form is isolated by conventional means, such as extraction with an organic solvent.

Salts of the compounds of Formula I may be interchanged by taking advantage of differential solubilities of the salts, volatilities or acidities of the acids, or by treating with the appropriately loaded ion exchange resin. For example, the interchange is effected by the reaction of a salt of a compound of Formula I with a slight stoichiometric excess of an acid of a lower pKa than the acid component of the starting salt. This conversion is carried out at a temperature between about 0° C. and the boiling point of the solvent being used as the medium for the procedure.

In summary the compounds of the present invention are made by the procedures (i) and (ii) outlined below.

(i) The process for preparing compounds of the formula:

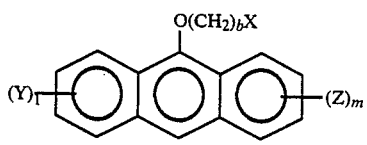
(I)

and the pharmaceutically acceptable acid addition salts thereof, wherein:
Y and Z are each independently halo, alkyl or alkoxy;
l and m are each independently integers of 0–4;
b is an integer of 2–12; and
X is selected from the group consisting of:
—$NR^1R^2$, —$NR^1(CH_2CH_2OH)$,

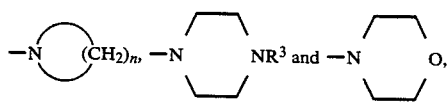

in which
$R^1$ and $R^2$ are independently H, alkyl or cycloalkyl;
$R^3$ is H, alkyl or $CH_2CH_2OH$; and
n is an integer of 3–7, comprises:

(a) reacting a compound of the formula:

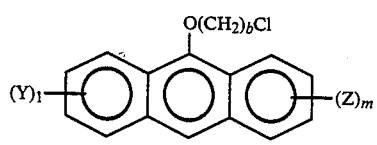

wherein Y, l, m and b are as defined above, with an appropriate amine of the formula HX, wherein X is as defined above; or (b) converting the free base of the compound of Formula I with an acid to a pharmaceutically acceptable acid addition salt; or (c) converting an acid addition salt of the compound of Formula I with a base to the corresponding free base; or (d) converting an acid addition salt of the compound of Formula I to another pharmaceutically acceptable acid addition salt.

(ii) Alternatively, a process for preparing a compound of Formula I, above, wherein X is $NH_2$, comprises (a) hydrolyzing a compound of the formula:

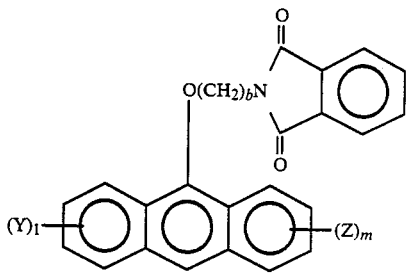

wherein Y, l, m and b are as defined herein, or;

(b) converting the free base of the compound of Formula I with an acid to a pharmaceutically acceptable acid addition salt; or (c) converting an acid addition salt of the compound of Formula I with a base to the corresponding free base; or (d) converting an acid addition salt of the compound of Formula I to another pharmaceutically acceptable acid addition salt.

Utility and Administration

The compounds of Formula I have been shown in standard laboratory tests to inhibit inflammation in mammals. Accordingly, the compounds of Formula I, their salts, and pharmaceutical compositions containing them, may be used in inhibiting, preventing, or controlling inflammation in mammals. Anti-inflammatory activity can be determined by the method described by C. M. Pearson in Proc. Soc. Exp. Biol. Med., 91: 95–101, (1956) utilizing adjuvant-induced arthritis in rats. This method is described in detail in Example 13 hereinbelow. The compounds of Formula I may also be useful in preventing, relieving or controlling the associated pain of various inflammatory conditions.

Administration of the active compounds and salts described herein can be effected via any medically acceptable mode of administration for agents which control inflammation and associated pain. These methods include but are not limited to oral, parenteral and otherwise systemic, or topical routes of administration. Oral or topical administration is preferred, depending of course, on the disorder being treated. The compounds are administered in a therapeutically effective amount either alone or in combination with a suitable pharmaceutically acceptable excipient.

Depending on the intended mode of administration, the compounds of this invention may be incorporated in any pharmaceutically acceptable dosage form, such as, for example, tablets, suppositories, pills, capsules, powders, liquids, suspensions, emulsions, aerosols, or the like. Preferable means of administration are unit dosage forms suitable for single administration of precise dosages, or sustained release dosage forms for continuous administration. Preferably the dosage form will include a pharmaceutically acceptable excipient and an active compound of Formula I, or a pharmaceutically acceptable salt thereof, and, in addition, may include other medicinal agents, pharmaceutical agents, carriers, excipients, adjuvants, stabilizers, etc. Depending on parameters such as mode of administration, type of composition, and activity of the compound, the pharmaceutical composition may contain 1-95 percent by weight active ingredient with the remainder being excipient.

For solid dosage forms, non-toxic solid carriers include but are not limited to, for example, pharmaceutical grades of mannitol, lactose, starch, magnesium stearate, sodium saccharin, the polyalkylene glycols, talcum, cellulose, glucose, sucrose, and magnesium carbonate. An example of a solid dosage form of the compounds of this invention is a suppository containing propylene glycol as the carrier. Liquid pharmaceutically administerable dosage forms can, for example, comprise a solution or suspension of an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences,* Mack Publishing Company, Easton, Pa., 16th Edition, 1980. The composition or formulation to be administered will, in any event, contain a quantity of the active compound(s) in an amount effective to alleviate the symptoms of the subject being treated.

For oral administration, a pharmaceutically acceptable non-toxic dosage form may contain any of the normally employed excipients, such as, for example pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like. Such dosage forms may contain 1%-95% active ingredient, preferably 25-70%.

For topical administration, an appropriate dosage form will comprise an effective amount of a compound of Formula I in admixture with a pharmaceutically acceptable non-toxic carrier. A suitable range of composition would be 0.1%-10%, preferably 1-2%, active ingredient, and the balance carrier. The concentration of active ingredient in pharmaceutical compositions suitable for topical application will vary depending upon the therapeutic activity of the particular active ingredient and the medical condition to be treated. Suitable dosage forms for topical application of the compounds of this invention include but are not limited to creams, ointments, lotions, emulsions and solutions.

For example, a suitable ointment for topical application of compounds of the instant invention may contain 15-45% by weight of a saturated fatty alcohol having 16 to 24 carbon atoms, such as cetyl alcohol, stearyl alcohol, behenyl alcohol, and the like, and 45-85% of a glycol solvent such as propylene glycol, polyethylene glycol, dipropylene glycol, and mixtures thereof. In addition, the ointment may contain 0-15% by weight of a plasticizer (e.g., polyethylene glycol, 1,2,6-hexanetriol, sorbitol, glycerol, and the like), 0-15% by weight of a coupling agent such as a saturated fatty acid having from 16 to 24 carbon atoms, (e.g., stearic acid, palmitic acid or behenic acid) a fatty acid amide (e.g., oleamide, palmitamide, stearamide or behenamide) or an ester of a fatty acid having from 16 to 24 carbon atoms, (e.g., sorbitol monostearate, polyethylene glycol monostearate, polypropylene glycol or the corresponding monoester of other fatty acids such as oleic acid and palmitic acid), and 0-20% by weight of a penetrant such as dimethyl sulfoxide or dimethylacetamide.

The amount of active compound administered will, of course, depend on the subject being treated, the severity of the affliction, the manner of administration and the judgment of the prescribing physician. However, a therapeutically effective dosage of compounds of the instant invention is in the range of 1-100 mg/kg/day, preferably about 10-30 mg/kg/day, and most preferably about 25 mg/kg/day. For an average 70 kg human, this would amount to 70 mg-7 g per day, or preferably about 1.5 g/day.

Preferred Embodiments

A subgroup of the family of compounds of the present invention are those compounds of Formula I where l and m are each independently 0-2, and X is $NR^1R^2$, where $R^1$ and $R^2$ are independently hydrogen, methyl or ethyl. Preferred embodiments of this subgroup are compounds of Formula I, and their pharmaceutically acceptable salts, wherein l and m are 0, and x is amino or dimethylamino. Especially preferred among these are compounds wherein b is an integer of 2 to 6, especially 3 and 4.

Particularly preferred are those compounds, and their salts, selected from the group consisting of:
1-(9-anthryloxy)-2-aminoethane;
1-(9-anthryloxy)-2-dimethylaminoethane;
1-(9-anthryloxy)-3-aminopropane;
1-(9-anthryloxy)-3-dimethylaminopropane;
1-(9-anthryloxy)-4-aminobutane;
1-(9-anthryloxy)-4-dimethylaminobutane;
1-(9-anthryloxy)-6-aminohexane.

The following preparations and examples serve to illustrate the invention; they should not be construed as in any way narrowing or limiting the scope of the invention as claimed.

PREPARATION 1

Preparation of 2-Ethylanthrone and Related Compounds of Formula A (a) aluminum chloride (270 g) was added in portions to a stirred mixture of phthalic anhydride (270 g) and ethyl benzene (1125 ml). After 4 hours the mixture was poured onto ice and concentrated hydrochloric acid (450 ml) was added. Excess ethylbenzene was removed by steam distillation, and the residual solution was cooled and filtered so as to afford 2-(4-ethylbenzoyl)-benzoic acid.

(b.1) A solution of 2-(4-ethylbenzoyl)benzoic acid in acetic acid (115 ml) and the dimethylformamide (115 ml) containing 10% palladium on carbon (4.9 g) was shaken in a hydrogen atmosphere at 60 p.s.i. for 6 hours. The solution was then filtered and the filtrate was added to water (2000 ml), producing a precipitate of 2-(4-ethylbenzyl)benzoic acid.

(b.2) (Alternative reduction procedure) Tin powder (15 g) is added to a solution of 2-(4-ethylbenzoyl)benzoic acid (3 g) in acetic acid (50 ml). Concentrated hydrochloric acid (5 ml) is added and the mixture is refluxed for 3 hours, then decanted from the undissolved tin, cooled, and diluted with water to afford a precipitate of 2-(4-ethylbenzyl)benzoic acid.

(c) 2-(4-Ethylbenzyl)benzoic acid (14 g) is added with stirring to sulphuric acid (200 ml) at 0° C. After 3 hours, the solution is poured into water and the product is extracted with ethyl acetate. The extract is washed with aqueous sodium carbonate, then dried and evaporated, to yield 2-ethylanthrone.

(d) In a similar manner, from the Friedel-Craft reaction of the appropriately substituted phthalic anhydrides and substituted benzenes of choice, as described in paragraphs (a)–(c) of this preparation, the following representative substituted anthrones of Formula A are prepared. (The reduction method of paragraph (b.2) is used when preparing halogenoanthrones):
3,6-dichloroanthrone;
3-chloroanthrone;
2-methylanthrone;
2-chloro-6-bromoanthrone;
2-ethylanthrone;
1,8-dimethylanthrone;
5-methylanthrone;
1,8-dimethoxyanthrone;
2-chloroanthrone;
2-methoxyanthrone;
3-methoxyanthrone;
2-methyl-7-methoxyanthrone;
1,4,5,7-tetramethylanthrone;
1,4,6-trimethoxyanthrone;
2,4-dimethoxyanthrone;
2,6-diethoxyanthrone;
3-chloro-4-methylanthrone;
7-bromoanthrone;
2-fluoro-5-methylanthrone;
4-methoxy-8-chloroanthrone;
2,7-dimethylanthrone;
2,3,5-triethylanthrone;
3,4,5,6-tetramethylanthrone.
8-methylanthrone;

PREPARATION 2

Alternative Synthesis of Halo-, Alkyl-, and Alkoxy-Anthrones (a) Preparation of 2- and 3-chloroanthrones.

Tin powder (100 g) and 2-chloroanthraquinone (70 g) were refluxed in acetic acid (500 ml) while concentrated hydrochloric acid (130 ml) was added over a period of 3 hours. The solution was cooled and the product was separated by filtration, and then chromatographed on silica gel, eluting with benzene:ether, so as to afford 2-chloroanthrone and 3-chloroanthrone.

(b) In a similar manner, but starting with the appropriately substituted anthraquinone of choice, the following representative substituted anthrones of Formula A are prepared:
3,6-dichloroanthrone;
3-chloroanthrone;
2-methylanthrone;
2-chloro-6-bromoanthrone;
2-ethylanthrone;
1,8-dimethylanthrone;
5-methylanthrone;
1,8-dimethoxyanthrone;
2-chloroanthrone;
2-methoxyanthrone;
3-methoxyanthrone;
2-methyl-7-methoxyanthrone;
1,4,5,7-tetramethylanthrone;
1,4,6-trimethoxyanthrone;
2,4-dimethoxyanthrone;
2,6-diethoxyanthrone;
8-methylanthrone;
2,4-dimethoxyanthrone;
2,6-diethoxyanthrone;
3-chloro-4-methylanthrone;
7-bromoanthrone;
2-fluoro-5-methylanthrone;
4-methoxy-8-chloroanthrone;
2,7-dimethylanthrone;
2,3,5-triethylanthrone;
3,4,5,6-tetramethylanthrone.

PREPARATION 3

Synthesis of ω-chloroethyl-p-toluenesulphonate (a) 2-Chloroethyl-p-toluenesulphonate.

Para-toluenesulphonyl chloride (20.5 g) was added to a mixture of 2-chloroethanol (8.6 g) and pyridine (50 ml). After stirring for one hour at 0° C., the mixture was added to ice and the organic phase was extracted with ether. The extract was washed with dilute hydrochloric acid, dried with magnesium sulphate, and evaporated, to yield 2-chloroethyl-p-toluenesulphonate.

(b) In a similar manner, using the corresponding longer chain ω-chloroalkanols, the following compounds are prepared:
3-chloropropyl-p-toluenesulphonate;
4-chlorobutyl-p-toluenesulphonate;
5-chloropentyl-p-toluenesulphonate;
6-chlorohexyl-p-toluenesulphonate;
7-chloroheptyl-p-toluenesulphonate;
8-chlorooctyl-p-toluenesulphonate;
9-chlorononyl-p-toluenesulphonate;
10-chlorodecyl-p-toluenesulphonate;
11-chlorodecyl-p-toluenesulphonate;
12-chlorodecyl-p-toluenesulphonate.

PREPARATION 4

Preparation of the anthryloxyalkyl chlorides of Formula B (a) Synthesis of 2-(9-anthryloxy)ethyl chloride.

2-Chloroethyl-p-toluenesulphonate (6.0 g) was added to a mixture of anthrone (5 g) and potassium carbonate (5 g) in dimethylformamide (130 ml). After stirring for 24 hours at 70° C., the reaction mixture was added to ether. The resultant solution was washed with dilute aqueous potassium hydroxide, dried with magnesium sulphate, and evaporated to yield a crude product which was chromatographed on silica gel, eluting with 4:1 hexane:ethyl acetate, to give 2-(9-anthryloxy)ethyl chloride.

(b) In a similar manner, but using the corresponding longer chain ω-chloroalkyl-p-toluene sulphonates, the following compounds are prepared:
3-(9-anthryloxy)propyl chloride;
4-(9-anthryloxy)butyl chloride;
5-(9-anthryloxy)pentyl chloride;
6-(9-anthryloxy)hexyl chloride;
7-(9-anthryloxy)heptyl chloride;
8-(9-anthryloxy)octyl chloride
9-(9-anthryloxy)nonyl chloride;
10-(9-anthryloxy)decyl chloride;
11-(9-anthryloxy)undecyl chloride;
12-(9-anthryloxy)dodecyl chloride.

(c) Following the procedure described in paragraph (a) of this example, but using instead a substituted anthrone and the same or a longer chain ω-chloroalkyl-p- toluene sulphonate, the following intermediate compounds of Formula B are prepared:
2-(3,6-dichloro-9-anthryloxy)ethyl chloride;
3-(3-chloro-9-anthryloxy)propyl chloride;
3-(2-methyl-9-anthryloxy)propyl chloride;
3-(2-chloro-6-bromo-9-anthryloxy)propyl chloride;
3-(2-ethyl-9-anthryloxy)propyl chloride;
4-(1,8-dimethyl-9-anthryloxy)butyl chloride;
4-(5-methyl-9-anthryloxy)butyl chloride;
4-(2-chloro-9-anthryloxy)butyl chloride;
4-(1,8-dimethoxy-9-anthryloxy)butyl chloride;
4-(3-methoxy-9-anthryloxy)butyl chloride;
5-(2-methyl-7-methoxy-9-anthyrloxy)pentyl chloride;
6-(1,4,5,7-tetramethyl-9-anthryloxy)hexyl chloride;
7-(1,4,6-trimethoxy-9-anthryloxy)heptyl chloride;
9-(2-methoxy-9-anthryloxy)nonyl chloride;
12-(8-methyl-9-anthryloxy)dodecyl chloride.

PREPARATION 5

Preparation of N-[(9-anthryloxy)alkyl]phthalimides of Formula C (a) N-[2-(9-anthryloxy)ethyl]phthalimide.

2-(9-Anthryloxy)ethyl chloride (7.0 g) and potassium phthalimide (2.8 g) were heated to 130° C. in dimethylformamide (70 ml) for 7 hours. The cooled solution was added to water and extracted with ethyl acetate. The extract was dried and evaporated to yield N-[2-(9-anthryloxy)ethyl]phthalimide.

(b) In a similar manner, but using the corresponding longer chain 9-anthryloxyalkyl chlorides, the following intermediate compounds of Formula C are prepared:
N-[3-(9-anthryloxy)propyl]phthalimide;
N-[4-(9-anthryloxy)butyl]phthalimide;
N-[5-(9-anthryloxy)pentyl]phthalimide;
N-[6-(9-anthryloxy)hexyl]phthalimide;
N-[7-(9-anthryloxy)heptyl]phthalimide;
N-[8-(9-anthryloxy)octyl]phthalimide;
N-[9-(9-anthryloxy)nonyl]phthalimide;
N-[10-(9-anthryloxy)decyl]phthalimide;
N-[11-(9-anthryloxy)undecyl]p]hthalimide;
N-[12-(9-anthryloxy)dodecyl]phthalimide.

(c) Following the procedures set forth in paragraphs (a) and (b) of this preparation, but using instead a substituted 9-anthryloxyalkyl chloride prepared according to the method of Preparation 4(c), above, the following representative intermediate compounds of Formula C are prepared:
N-[2-(3,6-dichloro-9-anthryloxy)ethyl]phthalimide;
N-[3-(3-chloro-9-anthryloxy)propyl]phthalimide;
N-[3-(2-methyl-9-anthryloxy)propyl]phthalimide;
N-[3-(2-chloro-6-bromo-9-anthryloxy)propyl]phthalimide;
N-[3-(2-ethyl-9-anthryloxy)propyl]phthalimide;
N-[4-(1,8-dimethyl-9-anthryloxy)butyl]phthalimide;
N-[4-(5-methyl-9-anthryloxy)butyl]phthalimide;
N-[4-(2-chloro-9-anthryloxy)butyl]phthalimide;
N-[4-(1,8-dimethoxy-9-anthryloxy)butyl]phthalimide;
N-[4-(3-methoxy-9-anthryloxy)butyl]phthalimide;
N-[5-(2-methyl-7-methoxy-9-anthryloxy)pentyl]phthalimide;
N-[6-(2,4,5,8-tetramethyl-9-anthryloxy)hexyl]phthalimide;
N-[7-(3,5,8-trimethoxy-9-anthryloxy)heptyl]phthalimide
N-[9-(2-methoxy-9-anthryloxy)nonyl]phthalimide;
N-[12-(8-methyl-9-anthryloxy)dodecyl]phthalimide.

EXAMPLE 1

Preparation of 1-(9-anthryloxy)-2-aminoethane and related compounds of Formula I (a) N-[2-(9-anthryloxy)ethyl]phthalimide (6.5 g) was refluxed for 3 hours in ethanol containing 85% hydrazine hydrate (3.0 ml). The solution was cooled and diluted with ethyl acetate. The resultant solution was washed with dilute aqueous potassium hydroxide, dried and evaporated. The crude product was chromatographed on 300 g silica gel, eluting with a solution of methylene chloride:methanol:ammonium hydroxide, 95:4:1, yielding 1-(9-anthryloxy)-2-aminoethane, which was converted to the maleate, mp 190°-195° C., according to the method of Example 3.

(b) Following the procedure described above in paragraph 1(a) of this Example, but substituting the appropriate N-[(9-anthryloxy)alkyl]phthalimide, whose preparation is described in Preparation 5, above, for the N-[2-(9-anthryloxy)ethyl]phthalimide, the following compounds of Formula I were prepared and converted to their corresponding pharmaceutically acceptable salts:
1-(9-anthryloxy)-3-aminopropane, as the hydrochloride, mp 235°-240° C.;
1-(9-anthryloxy)-4-aminobutane, as the phosphate, mp 184° C.;
1-(9-anthryloxy)-6-aminohexane, as the phosphate, mp 163° C.;
1-(9-anthryloxy)-8-aminooctane, as the phosphate, mp 149° C.

(c) In a similar manner, the following compounds are prepared:
1-(9-anthryloxy)-5-aminopentane;
1-(9-anthryloxy)-7-aminoheptane;
1-(9-anthryloxy)-9-aminononane;
1-(9-anthryloxy)-10-aminodecane;
1-(9-anthryloxy)-11-aminoundecane;
1-(9-anthryloxy)-12-aminododecane.

(d) Similarly, but substituting the appropriate N-[substituted(9-anthryloxy)alkyl]phthalimide prepared as described in Preparation 4(c), above, for the N-[2-(9-anthryloxy)ethyl]phthalimide, the following compounds of Formula I are obtained:
1-(3,6-dichloro-9-anthryloxy)-2-aminoethane;
1-(3-chloro-9-anthryloxy)-3-aminopropane;
1-(2-methyl-9-anthryloxy)-3-aminopropane;
1-(2-chloro-6-bromo-9-anthryloxy)-3-aminopropane;
1-(2-ethyl-9-anthryloxy)-3-aminopropane;
1-(1,8-dimethyl-9-anthryloxy)-4-aminobutane;
1-(5-methyl-9-anthryloxy)-4-aminobutane;
1-(2-chloro-9-anthryloxy)-4-aminobutane;
1-(1,8-dimethoxy-9-anthryloxy)-4-aminobutane;
1-(3-methoxy-9-anthryloxy)-4-aminobutane;
1-(2-methyl-7-methoxy-9-anthryloxy)-5-aminopentane;
1-(1,4,5,7-tetramethyl-9-anthryloxy)-6-aminohexane;
1-(1,4,6-trimethoxy-9-anthryloxy)-7-aminoheptane;
1-(2-methoxy-9-anthryloxy)-9-aminononane;
1-(8-methyl-9-anthryloxy)-12-aminododecane.

EXAMPLE 2

Preparation of 1-(9-anthryloxy)-2-dimethylaminoethane and related compounds of Formula I (a) 2-(9-Anthryloxy)ethyl chloride (5.0 g) was heated for 5 hours at 90° C. in methylene glycol (50 ml) containing dimethylamine (4.0 g) using a dry ice condenser. The solution was cooled and added to water. The resulting mixture was extracted with ethyl acetate, and the extract dried and evaporated. The crude product was chromatographed on 100 g silica gel, eluting with a solution of methylene chloride:methanol:ammonium hydroxide, 95:5:1, to yield 1-(9-anthryloxy)-2-dimethylaminoethane, which was converted to the maleate, mp 132°–134° C.

(b) Following the procedure described in paragraph (a) above, but starting with the appropriate longer chain 9-anthryloxyalkyl chloride whose synthesis is described in Preparation 4(b), above, the following compounds of Formula I were prepared:

1-(9-anthryloxy)-3-dimethylaminopropane, as the phosphate, mp 196°–200° C.;
1-(9-anthryloxy)-4-dimethylaminobutane, as the phosphate, mp 165°–166° C.;
1-(9-anthryloxy)-6-dimethylaminohexane, as the phosphate, mp 126° C.;
1-(9-anthryloxy) 8-dimethylaminooctane, as the phosphate, mp 100° C.

(c) In a similar manner, related substituted compounds of Formula I are prepared from substituted (9-anthryloxy)alkyl chlorides synthesized according to the method described in Preparation 4(c), above. These include, without limitation:

1-(3,6-dichloro-9-anthryloxy)-2-dimethylaminoethane;
1-(3-chloro-9-anthryloxy)-3-dimethylaminoaminopropane;
1-(2-methyl-9-anthryloxy)-3-dimethylaminopropane;
1-(2-chloro-6-bromo-9-anthryloxy)-3-dimethylaminopropane;
1-(2-ethyl-9-anthryloxy)-3-dimethylaminopropane;
1-(1,8-dimethyl-9-anthryloxy)-4-dimethylaminobutane;
1-(5-methyl-9-anthryloxy)-4-dimethylaminobutane;
1-(1,8-dimethoxy-9-anthryloxy)-4-dimethylaminobutane;
1-(2-chloro-9-anthryloxy)-4-dimethylaminobutane;
1-(3-methoxy-9-anthryloxy)-4-dimethylaminobutane;
1-(2-methyl-7-methoxy-9-anthryloxy)-5-dimethylaminopentane;
1-(1,4,5,7-tetramethyl-9-anthryloxy)-6-dimethylaminohexane;
1-(1,4,6-trimethoxy-9-anthryloxy)-7-dimethylaminoheptane;
1-(2-methoxy-9-anthryloxy)-9-dimethylaminononane;
1-(8-methyl-9-anthryloxy)-12-dimethylaminododecane.

(d) Similarly, but substituting an appropriate cyclic or acylic amine for the N,N-dimethylamine, the following representative compounds of Formula I are prepared:

1-(9-anthryloxy)-2-(2-hydroxyethylamino)ethane
1-(9-anthryloxy)-3-pyrrolidinopropane;
1-(9-anthryloxy)-3-(N-methyl-N-ethyl)aminopropane;
1-(9-anthryloxy)-3-(4-ethylpiperazino)propane;
1-(9-anthryloxy)-3-diisopropylaminopropane;
1-(9-anthryloxy)-4-piperadinobutane;
1-(9-anthryloxy)-4-(N-methyl-N-n-butylamino)butane;
1-(9-anthryloxy)-4-morpholinobutane;
1-(9-anthryloxy)-5-(4-methylpiperazino)pentane;
1-(9-anthryloxy)-3-ethylaminopropane;
1-(9-anthryloxy)-4-azetidinobutane;
1-(9-anthryloxy)-6-(4-(2-hydroxyethyl)piperazino)hexane;
1-(9-anthryloxy)-8-ethylaminooctane;
1-(9-anthryloxy)-9-(N-methyl-N-ethylamino)nonane;
1-(9-anthryloxy)-10-di-n-propylaminodecane;
1-(9-anthryloxy)-12-pyrrolidinododecane.
1-(3,6-dichloro-9-anthryloxy)-2-(2-hydroxyethylamino)ethane;
1-(3-chloro-9-anthryloxy)-3-pyrrolidinopropane;
1-(2-methyl-9-anthryloxy)-3-(4-ethylpiperazino)propane;
1-(2-chloro-6-bromo-9-anthryloxy)-3-diethylaminopropane;
1-(1,8-dimethyl-9-anthryloxy)-3-methylaminopropane;
1-(2-ethyl-9-anthryloxy)-3-azetidinopropane;
1-(5-methyl-9-anthryloxy)-4-ethylaminobutane;
1-(2-chloro-9-anthryloxy)-4-piperazinobutane;
1-(3-methoxy-9-anthryloxy)-4-(2-hydroxyethylamino)butane;
1-(1,8-dimethoxy-9-anthryloxy)-5-(methyl-n-butylamino)butane;
1-(2-methyl-7-methoxy-9-anthryloxy)-5-di-n-propylaminopentane;
1-(1,4,5,7-tetramethyl-9-anthryloxy)-6-(4-methylpyrrolidinohexane;
1-(1,4,6-trimethoxy-9-anthryloxy)-7-piperazinoheptane;
1-(2-methoxy-9-anthryloxy)-9-diethylaminononane;
1-(9-methyl-9-anthryloxy)-12-pyrrolidinododecane;
1-(1,8-dimethyl-9-anthryloxy)-12-pyrrolidinododecane.

EXAMPLE 3

Conversion of Free Base to Salt

A twofold stoichiometric excess of 3% phosphoric acid in methanol is added to a methanolic solution of 1.0 g. of 1-(9-anthryloxy)-3-dimethylaminopropane. Diethyl ether is added until precipitation is complete. The product is filtered, washed with ether, air dried and recrystallized to give 1-(9-anthryloxy)-3-dimethylaminopropane phosphate, m.p. 196°–200° C.

In a similar manner, all compounds of Formula I in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE 4

Conversion of Salt to Free Base 1.0 g of 1-(9-anthryloxy)-2-aminoethane maleate suspended in 50 ml of ether is stirred with a twofold stoichiometric excess of dilute aqueous potassium carbonate solution until the salt is completely dissolved. The organic layer is then separated, washed twice with water, dried over magnesium sulfate and evaporated to yield 1-(9-anthryloxy)-2-aminoethane as the free base.

EXAMPLE 5

Direct interchange of acid addition salts 1-(9-anthryloxy)-3-aminopropane acetate (1.0 g) is dissolved in 50 ml water containing a stoichiometric equivalent to sulfuric acid, and the solution evaporated to dryness. The product is suspended in ethanol and filtered, air dried and recrystallized from methanol/acetone to yield 1-(9-anthryloxy)-3-aminopropane bisulfate.

In a similar manner interchanges between other acid addition salts of compounds of Formula I can be made by treating with an appropriate inorganic or organic acid.

EXAMPLES 6-11

In Examples 6 through 11, the active ingredient is 1-(9-anthryloxy)-4-aminobutane phosphate; however other compounds of Formula I and the pharmaceutically acceptable salts thereof may be substituted therein:

EXAMPLE 6

| Ingredients | Quantity per tablet, mgs. |
|---|---|
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 7

| Ingredients | Quantity per tablet, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE 8

| Ingredients | Quantity per tablet, mgs. |
|---|---|
| Active ingredient | 108 |
| lactose | 15 |
| cornstarch | 25 |
| magnesium stearate | 2 |

The above ingredients are mixed and introduced into a hard-shell gelatin capsule.

EXAMPLE 9

| Ingredients | Quantity per tablet, mgs. |
|---|---|
| Active ingredient | 150 |
| lactose | 92 |

The above ingredients are mixed and introduced into a hard-shell gelatin capsule.

EXAMPLE 10

A solution preparation buffered to a pH of 7 is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| distilled water | q.s. to 100 ml |

EXAMPLE 11

A topical formulation is prepared as follows. The composition contains:

| | % wt./wt. |
|---|---|
| Active ingredient | 0.5 |
| Methyl paraben | 0.025 |
| Propyl paraben | 0.015 |
| Sodium lauryl sulfate | 1.0 |
| Propylene glycol | 12.0 |
| Stearyl alcohol | 25.0 |
| White petrolatum | 25.0 |
| Purified water qs. ad. | 100.0 |

The stearyl alcohol and white petrolatum are heated on a steam bath to about 75° C. The other ingredients, previously dissolved in the water and warmed to 75° C., are added with stirring. Stirring is continued until the mixture congeals.

EXAMPLE 13

Determination of Anti-Inflammatory Activity Utilizing Adjuvant-Induced Arthritis In The Rat Protocol:

This procedure is a modification of a system initially described by Pearson, C. M., *Proc. Soc. Exp. Biol. Med.*, 91: 95-101 (1956).

Female Simonsen albino rats weighing 160-180 g received 0.1 ml of a suspension in paraffin oil of heat-killed M. butyricum (10 mg/ml) by means of an intradermal injection into the proximal ¼ of the tail on day 0. Beginning on day 1, the test material was administered orally in an aqueous vehicle (0.5 ml/dose) twice each day for 17 days. On day 18 the intensity of the swelling of the four foot pads and tail was determined utilizing a scoring system in which the swelling in the four paws was scored 0-4 for each paw and the tail swelling was scored 0-3, such that the total maximum score was 19. The compounds of the present invention show anti-inflammatory activity when tested by this method.

What is claimed is:

1. A compound of the formula:

$$(Y)_l \text{-anthracene-} O(CH_2)_b X \text{-} (Z)_m$$

and the pharmaceutically acceptable acid addition salts thereof, wherein:

Y and Z are each independently halo, alkyl or alkoxy;
l and m are each independently integers of 0-4;
b is an integer of 2-12; and
x is selected from the group consisting of:
—$NR^1R^2$, —$NR^1(CH_2CH_2OH)$, $$-N\underbrace{(CH_2)_n}, \quad -N\underbrace{\phantom{xx}}NR^3 \text{ and } -N\underbrace{\phantom{xx}}O,$$

in which
$R^1$ and $R^2$ are each independently H, alkyl or cycloalkyl;
$R^3$ is H, alkyl or $CH_2CH_2OH$; and n is an integer of 3-7.

2. The compound of claim 1, and the pharmaceutically acceptable acid addition salts thereof wherein:
l and m are each independently integers of 0-2; and
X is $-NR^1R^2$ where $R^1$ and $R^2$ are each independently hydrogen, methyl or ethyl.

3. The compound of claim 2, and the pharmaceutically acceptable acid addition salts thereof wherein:
l and m are 0;
b is an integer of 2-6; and
X is $-NH_2$ or $-N,N$-dimethyl.

4. The compound of claim 3 wherein b is 2 and X is $-NH_2$, namely 1-(9-anthryloxy)-2-aminoethane, and the pharmaceutically acceptable acid addition salts thereof.

5. The compound of claim 3 wherein b is 2 and X is $-N,N$-dimethyl, namely
1-(9-anthryloxy)-2-dimethylaminoethane, and the pharmaceutically acceptable acid addition salts thereof.

6. The compound of claim 3 wherein b is 3 and X is $-NH_2$, namely 1-(9-anthryloxy)-3-aminopropane, and the pharmaceutically acceptable acid addition salts thereof.

7. The compound of claim 3 wherein b is 3 and X is $-N,N$-dimethyl, namely
1-(9-anthryloxy)-3-dimethylaminopropane, and the pharmaceutically acceptable acid addition salts thereof.

8. The compound of claim 3 wherein b is 4 and X is $-NH_2$, namely 1-(9-anthryloxy)-4-aminobutane, and the pharmaceutically acceptable acid addition salts thereof.

9. The compound of claim 3 wherein b is 4 and X is $-N,N$-dimethyl, namely
1-(9-anthryloxy)-4-dimethylaminobutane, and the pharmaceutically acceptable acid addition salts thereof.

10. The compound of claim 3 wherein b is 5 and X is $NH_2$, namely 1-(9-anthryloxy)-5-aminopentane, and the pharmaceutically acceptable acid addition salts thereof.

11. The compound of claim 3 wherein b is 5 and X is $-N,N$-dimethyl, namely
1-(9-anthryloxy)-5-dimethylaminopentane, and the pharmaceutically acceptable acid addition salts thereof.

12. The compound of claim 3 wherein b is 6 and X is $-NH_2$, namely
1-(9-anthryloxy)-6-aminohexane, and the pharmaceutically acceptable acid addition salts thereof.

13. The compound of claim 3 wherein b is 6 and X is $-N,N$-dimethyl, namely
1-(9-anthryloxy)-6-dimethylaminohexane, and the pharmaceutically acceptable acid addition salts thereof.

14. A pharmaceutical composition useful for preventing, reducing or inhibiting inflammation which comprises a therapeutically effective amount of a compound of claim 1 or a pharmaceutically acceptable acid addition salt thereof in admixture with one or more pharmaceutically acceptable excipients.

15. A method of preventing, reducing or inhibiting inflammation which method comprises adminstering to a mammal in need of such treatment a therapeutically effective amount of a compound of claim 1 or a pharmaceutically acceptable acid addition salt thereof.

* * * * *